United States Patent
Leypoldt et al.

(10) Patent No.: US 8,975,240 B2
(45) Date of Patent: Mar. 10, 2015

(54) PERITONEAL DIALYSIS SOLUTIONS COMPRISING GLUCOSE POLYMERS

(75) Inventors: John Kenneth Leypoldt, Libertyville, IL (US); Clifford J. Holmes, Glenview, IL (US); Sujatha Karoor, Lake Forest, IL (US); Catherine M. Hoff, Lake Bluff, IL (US); Leo Martis, Long Grove, IL (US); Rahul Tandon, Grayslake, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/419,701

(22) Filed: Mar. 14, 2012

(65) Prior Publication Data

US 2012/0238525 A1  Sep. 20, 2012

Related U.S. Application Data

(60) Provisional application No. 61/454,251, filed on Mar. 18, 2011.

(51) Int. Cl.
| | | |
|---|---|---|
| A61K 31/716 | (2006.01) | |
| A61K 31/718 | (2006.01) | |
| C08L 3/02 | (2006.01) | |
| A61K 31/717 | (2006.01) | |

(52) U.S. Cl.
CPC ............ *A61K 31/717* (2013.01); *A61K 31/716* (2013.01); *A61K 31/718* (2013.01); *C08L 3/02* (2013.01)
USPC ................................. 514/58; 514/54; 514/60

(58) Field of Classification Search
CPC ....... A61K 31/716; A61K 31/718; C08L 3/02
See application file for complete search history.

(56) References Cited

U.S. PATENT DOCUMENTS

| | | | |
|---|---|---|---|
| 4,445,938 | A | 5/1984 | Verwaerde et al. |
| 4,761,237 | A | 8/1988 | Alexander et al. |
| 4,886,789 | A | 12/1989 | Milner |
| 5,424,302 | A | 6/1995 | Nitsch |
| 5,837,060 | A | 11/1998 | Fouache |
| 6,068,705 | A | 5/2000 | Tang et al. |
| 6,077,836 | A | 6/2000 | Milner |
| 6,248,726 | B1 | 6/2001 | Alsop et al. |
| 6,284,140 | B1 | 9/2001 | Sommermeyer |
| 6,306,836 | B1 | 10/2001 | Martis |
| 6,348,264 | B1 | 2/2002 | Abou-Nemeh et al. |
| 6,630,586 | B1 | 10/2003 | Fouache |
| 6,747,064 | B2 | 6/2004 | Emanuele et al. |
| 2006/0128658 | A1 | 6/2006 | Martis et al. |
| 2009/0239821 | A1* | 9/2009 | Johnson et al. ................. 514/54 |

FOREIGN PATENT DOCUMENTS

| | | |
|---|---|---|
| EP | 0 076 355 | 4/1983 |
| EP | 0153164 | 8/1985 |
| EP | 0207676 | 1/1987 |
| EP | 0667356 | 8/1995 |
| GB | 2132914 A | 7/1984 |
| GB | 2247242 | 2/1992 |
| WO | 82/03329 | 10/1982 |

OTHER PUBLICATIONS

International Search Report and Written Opinion for International Application No. PCT/US2012/028999 dated Jun. 13, 2012.
"European Peritoneal Dialysis Meeting 2011", 10th European Peritoneal Dialysis Meeting 2011, vol. 10th, Oct. 21, 2011, pp. 1-100, XP007920683.
Gross, M.L. et al., "A comparison of glucose polymer and dextrose containing dialysate in CAPD patients", Trans Am Soc Artif Intern Organs, 30: 483-5, 1984.
Jeloka, et al., Peritoneal Dialysis International, vol. 26(3), pp. 336-340 (2006).
Mistry, C. et al., "Ultrafiltration with an isosmotic solution during long peritoneal dialysis exchanges", Lancet, 2: 178-82, 1987.
Mistry, C. "Glucose Polymer as an Osmotic Agent in Continuous Peritoneal Dialysis", MD Thesis. London, England, University of London, 1988 (Abstract and Table of Contents Only).
Mistry, C. et al., "Can ultrafiltration occur with a hypo-osmolar solution in peritoneal dialysis?: The role for 'colloid' osmosis", Clin Sci (Loud), 85: 495-500, 1993.
Nishimura, et al., "Molecular weight of polydisperse icodextrin effects its oncotic contribution to water transport", J Artif, Organs (2008) vol. 11, pp. 165-169.
Plum, J. et al., Am. J. Kidney Dis., vol. 39, pp. 862-871 (2002).
Rippe, B. et al., Kidney Int., vol. 35, pp. 1234-1244 (1989).
Rippe, B. et al., "Theoretical analysis of osmotic agents in peritoneal dialysis. What size is an ideal osmotic agent?", Perit Dial Int, 16 Suppl 1: S97-103, 1996.
Rippe, B. et al., "Computer simulations of ultrafiltration profiles for an icodextrin-based peritoneal fluid in CAPD", Kidney Int, 57: 2546-56, 2000.
Rubin, J. et al., "Evaluation of a polymer dialysate", Trans Am Soc Artif Intern Organs, 29: 62-6, 1983.
Rubin, J. et al., "Substitution of a starch polymer for glucose in peritoneal dialysis", Nephron, 39: 40-6, 1985.
Vonesh, E.F. et al., "Modeling of icodextrin in PD Adequest", 2.0. Perit Dial Int, 26: 475-81, 2006.
Winchester, J.F. et al., "A comparions of glucose polumer and dextrose as osmotic agents in CAPD. In: Frontiers in Peritoneal Dialysis", edited by Maher, J. F. & Winchester, J. F., New York, Field, Rich and Associates, Inc, 1986, pp. 231-240.

(Continued)

*Primary Examiner* — Yong Chu
*Assistant Examiner* — Yih-Horng Shiao
(74) *Attorney, Agent, or Firm* — K&L Gates LLP (57) ABSTRACT

Peritoneal dialysis solutions including a glucose polymer and methods of using the dialysis solutions are disclosed herein. In a general embodiment, the peritoneal dialysis solution includes a glucose polymer in an amount to provide an increased ultrafiltration fluid volume for a given amount of carbohydrate absorbed compared to conventional dialysis solutions containing icodextrin as the active pharmaceutical ingredient. The increased ultrafiltration fluid volume for a given amount of carbohydrate absorbed is obtained by providing specific combinations of weight-average molecular weight, polydispersity index and concentration of the glucose polymer in the dialysis solution.

37 Claims, 6 Drawing Sheets

(56) References Cited

OTHER PUBLICATIONS

Garcia-Lopez, E. et al., "Determination of High and Low Molecular Weight Molecules of Icodextrin in Plasma and Dialysate, Using Gel Filtration Chromatography, in Peritoneal Dialysis Patients", Peritoneal Dialysis International, vol. 25, pp. 181-191.

Garcia-Lopez, E. et al., "Icodextrin Metabolisn and Alpha-Amylase Activity in Nonuremic Rats Undergoing Chronic Peritoneal Dialysis", Peritoneal Dialysis International, vol. 27, pp. 415-423.

Garcia-Lopez, E. et al. "Icodextrin Metabolities in Peritoneal Dialysis", Peritoneal Dialysis International, vol. 29, pp. 370-376.

Mistry, Chandra D., et al., "New Osmotic Agents for Peritoneal Dialysis: Where We Are and Where We're Going," Seminars in Dialysis—vol. 4, No. 1 Jan.-Mar. 1991, pp. 9-12.

Mistry, C.D., et al., "Kinetic and Clinical Studies of β2-Microglobulin in Continuous Ambulatory Peritoneal Dialysis: Influence of Renal and Enhanced Peritoneal Clearances Using Glucose Polymer," Nephrology Dialysis Transplantation (1990) 5: 513-519.

Mistry, C.D., et al., "Single daily overnight (12-h dwell) use of 7.5% glucose polymer MMw 18 700; Mn 7300) + 0.35% glucose solution: a 3-month study," Nephrology Dialysis Transplantation (1993) 9: 443-447.

Mistry, C.D., et al., "Glucose Polymer (GP) as an Osmotic Agent in Continuous Ambulatory Peritoneal Dialysis," Medical Research Society Communications, Manchester Royal Infirmary, Manchester UK, pp. 12-13, not dated.

International Preliminary Report on Patentability mailed on May 23, 2013 for corresponding International Application No. PCT/US2012/028999.

Response to Written Opinion dated Apr. 19, 2013 for corresponding International Application No. PCT/US2012/028999.

European Office Action for European Application No. 12 710 844.7, dated Jul. 22, 2014.

\* cited by examiner

PERITONEAL DIALYSIS SOLUTIONS COMPRISING GLUCOSE POLYMERS

CROSS REFERENCE TO RELATED APPLICATIONS

This application claims the benefit of U.S. Provisional Patent Application Ser. No. 61/454,251 filed on Mar. 18, 2011, the entire disclosure of which is hereby incorporated by reference.

BACKGROUND

The present disclosure relates generally to medical treatments. More specifically, the present disclosure relates to solutions for peritoneal dialysis therapy.

Due to disease or other causes, a person's renal system can fail. In renal failure of any cause, there are several physiological derangements. The balance of water, minerals and the excretion of daily metabolic load are no longer possible in renal failure. During renal failure, toxic end products of nitrogen metabolism (e.g., urea, creatinine, uric acid, and others) can accumulate in blood and tissues.

Kidney failure and reduced kidney function have been conventionally treated with dialysis therapies. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

In peritoneal dialysis ("PD"), the osmotic agent is used in the dialysis solution to maintain the osmotic gradient required to cause transport of water and toxic substances across the peritoneum into the dialysis solution. One of the difficulties encountered in PD therapy is providing a dialysate that includes a suitable osmotic agent. Achieving a sufficient osmotic gradient is required.

Presently, the osmotic agent that is most commercially used is glucose. Glucose is fairly safe and is readily metabolized if it enters the blood. However, one of the problems with glucose is that it is readily taken up by the blood from the dialysate. Because glucose crosses the peritoneum so rapidly, the osmotic gradient is dissipated within two to three hours of infusion. This can reverse the direction of ultrafiltration, causing water to be reabsorbed from the dialysate toward the end of the time allowed for the exchange.

Glucose also presents other problems for dialysis treatment. For example, because glucose is taken up so rapidly by the blood, it can represent a large proportion of the patient's energy intake. While this may not significantly affect a non-diabetic patient, it can represent a severe metabolic burden to a patient whose glucose tolerance is already impaired. Glucose can also cause problems with respect to hyperglycemia and obesity. Finally, heat sterilization of glucose can result in unwanted glucose degradation products.

Ultrafiltration characteristics of PD solutions can be improved during long dwells by replacing glucose with large molecular weight substances such as glucose polymers. Dialysis solutions containing certain glucose polymers, i.e., icodextrin, are commercially available and have been found to be useful in treating patients with end stage renal disease.

Summary

The present disclosure is directed to PD solutions including a glucose polymer and methods of using the dialysis solutions. In a general embodiment, the PD solutions include one or more glucose polymers having specific characteristics and in an amount that provides an increased ultrafiltration ("UF") fluid volume for a given amount of carbohydrate ("CHO") absorbed compared to conventional dialysis solutions containing icodextrin as the active pharmaceutical ingredient ("API"). The increased UF fluid volume for a given amount of CHO absorbed is obtained by providing specific combinations of weight-average molecular weight ("Mw"), polydispersity ("PolyD") index (e.g., Mw/Mn) and concentration (e.g., by weight/volume percent ("w/v")) of the glucose polymers in the dialysis solutions. The dialysis solutions can be sterilized using any suitable sterilizing methods.

In any embodiments of the dialysis solutions disclosed herein, the PD solutions can include one or more additional dialysis components such as buffers, electrolytes or a combination thereof. The buffer can be bicarbonate, lactate, pyruvate, acetate, citrate, amino acids, peptides, an intermediate of the KREBS cycle or a combination thereof. The electrolytes can be calcium, magnesium, sodium, potassium, chloride or a combination thereof.

In an alternative embodiment, the present disclosure provides a method of preparing a PD solution. The method includes selecting a specific Mw, a PolyD index and a w/v concentration of the glucose polymer to be used in the dialysis solution, and providing the glucose polymer at the specified PolyD index, molecular weight and w/v concentration in a dialysis solution.

In yet another embodiment, the present disclosure provides a method of providing PD to a patient in need of same. The method includes selecting a specific Mw, a PolyD index and a w/v concentration of the glucose polymer to be used in the dialysis solution, providing the glucose polymer at the specified PolyD index, molecular weight and w/v concentration in a dialysis solution, and administering the dialysis solution to the patient.

An advantage of the present disclosure is to provide an improved PD solution including glucose polymers.

Another advantage of the present disclosure is to provide a PD solution capable of providing an increased UF fluid volume for a given amount of CHO absorbed compared to conventional dialysis solutions containing icodextrin as the API.

Still another advantage of the present disclosure is to provide a method of making an improved PD solution containing a glucose polymer.

Yet another advantage of the present disclosure is to provide an improved method of administering a PD solution containing a glucose polymer.

Additional features and advantages are described herein, and will be apparent from the following Detailed Description and the figures.

DETAILED DESCRIPTION

PD solutions including a glucose polymer and methods of preparing and administering the dialysis solutions are disclosed herein. In a general embodiment, the PD solutions include a glucose polymer having specific characteristics and in an amount that provides an increased UF fluid volume for a given amount of CHO absorbed compared to conventional dialysis solutions containing icodextrin as the API. The increased UF fluid volume for a given amount of CHO absorbed is obtained by providing a specific combination of Mw, PolyD index and concentration of the glucose polymers in the dialysis solutions. The limitation of CHO absorption in such solutions is important to limit clinical side effects. For example, it is desirable to limit CHO absorbance in order to minimize adverse metabolic effects such as a build-up of maltose and other glucose polymer metabolites in the blood or caloric overload.

It has been surprisingly found that reducing the PolyD index of a glucose polymer in a dialysis solution to below about 2.5 in conjunction with specific combinations of Mw and concentrations of the glucose polymer provides conditions that result in increased UF compared with conventional dialysis solutions containing icodextrin as the API. These results are improved over combinations of glucose polymer concentrations and average molecular weight profiles having PolyD indexes greater than 2.5 but only over specific concentration ranges that are dependent on Mw. Computer modeling simulations performed, as discussed in more detail in the Examples, have demonstrated that the specific combinations of Mw, PolyD index and concentration of glucose polymers are able to achieve increased UF fluid volume for a given amount of CHO absorbed compared to corresponding conventional dialysis solutions containing icodextrin as the API.

In any embodiment of the dialysis solutions disclosed herein, the glucose polymers can be, for example metabolizable glucose polymers such as oligosaccharides, polysaccharides, maltodextrin or starch hydrolysates. In an embodiment, the present disclosure provides a dialysis solution including from about 7% w/v to about 10.5% w/v glucose polymer. The glucose polymer has a weight-average molecular weight of y and a PolyD index of z, wherein: if y=about 7,500 daltons to about 8,500 daltons, then z=about 1.5 to about 1.7, if y=about 8,501 daltons to about 9,500 daltons, then z=about 1.7 to about 1.9, or if y=about 10,500 daltons to about 11,500 daltons, then z=about 2.1 to about 2.3.

In another embodiment, the present disclosure provides a dialysis solution including from about 7% w/v to about 15% w/v glucose polymer. The glucose polymer has a weight-average molecular weight of y and a PolyD index of z, wherein: if y=about 8,500 daltons to about 9,500 daltons, then z=about 1.5 to about 1.7, if y=about 9,501 daltons to about 10,500 daltons, then z=about 1.5 to about 1.9, if y=about 10,501 daltons to about 11,500 daltons, then z=about 1.5 to about 2.1, if y=about 11,501 daltons to about 12,500 daltons, then z=about 1.7 to about 2.3, if y=about 12,501 daltons to about 13,500 daltons, then z=about 1.9 to about 2.5, or if y=about 13,501 daltons to about 14,500 daltons, then z=about 2.1 to about 2.5.

In yet another embodiment, the present disclosure provides a dialysis solution including from about 8% w/v to about 15% w/v glucose polymer. The glucose polymer has a weight-average molecular weight of y and a PolyD index of z, wherein: if y=about 11,500 daltons to about 12,500 daltons, then z=about 1.5 to about 1.7, if y=about 12,501 daltons to about 13,500 daltons, then z=about 1.5 to about 1.9, if y=about 13,501 daltons to about 14,500 daltons, then z=about 1.5 to about 2.1, if y=about 14,501 daltons to about 15,500 daltons, then z=about 1.5 to about 2.5, if y=about 15,501 daltons to about 16,500 daltons, then z=about 1.7 to about 2.5, if y=about 16,501 daltons to about 17,500 daltons, then z=about 1.9 to about 2.5, if y=about 17,501 daltons to about 18,500 daltons, then z=about 2.1 to about 2.5, or if y=about 18,501 daltons to about 19,500 daltons, then z=about 2.3 to about 2.5.

In still another embodiment, the present disclosure provides a dialysis solution including from about 9% w/v to about 15% w/v glucose polymer. The glucose polymer has a weight-average molecular weight of y and a PolyD index of z, wherein: if y=about 15,501 daltons to about 16,500 daltons, then z=about 1.5 to about 1.7, if y=about 16,501 daltons to about 17,500 daltons, then z=about 1.5 to about 1.9, if y=about 17,501 daltons to about 18,500 daltons, then z=about 1.5 to about 2.1, if y=about 18,501 daltons to about 19,500 daltons, then z=about 1.5 to about 2.3, if y=about 19,501 daltons to about 20,500 daltons, then z=about 1.7 to about 2.5, if y=about 20,501 daltons to about 21,500 daltons, then z=about 1.7 to about 2.5, if y=about 21,501 daltons to about 22,500 daltons, then z=about 1.9 to about 2.5, or if y=about 22,501 daltons to about 23,500 daltons, then z=about 2.3 to about 2.5.

In an alternative embodiment, the present disclosure provides a dialysis solution including from about 10% w/v to about 15% w/v glucose polymer. The glucose polymer has a weight-average molecular weight of y and a PolyD index of z, wherein: if y=about 19,501 daltons to about 20,500 daltons, then z=about 1.5 to about 1.7, if y=about 20,501 daltons to about 21,500 daltons, then z=about 1.5 to about 1.7, if y=about 21,501 daltons to about 22,500 daltons, then z=about 1.5 to about 1.9, if y=about 22,501 daltons to about 23,500 daltons, then z=about 1.5 to about 2.1, or if y=about 23,501 daltons to about 24,500 daltons, then z=about 1.7 to about 2.1 or about 2.3 to about 2.5.

In another embodiment, the present disclosure provides a dialysis solution including from about 7% w/v to about 12.5% w/v glucose polymer. The glucose polymer has a weight-average molecular weight of y and a PolyD index of z, wherein: if y=about 9,500 daltons to about 10,500 daltons, then z=about 1.9 to about 2.1, or if y=about 11,500 daltons to about 12,500 daltons, then z=about 2.3 to about 2.5.

In yet another embodiment, the present disclosure provides a dialysis solution including from about 13% w/v to about 15% w/v glucose polymer. The glucose polymer having a weight-average molecular weight of y and a PolyD index of z, wherein: if y=about 23,500 daltons to about 24,500 daltons, then z=about 1.5 to about 1.7.

In an embodiment, a method of preparing an improved PD solution includes selecting a specific Mw, a PolyD index and a w/v concentration of a glucose polymer to be used in the dialysis solution, and providing the glucose polymer at the specified PolyD index, molecular weight and w/v concentration to make the dialysis solution.

The dialysis solutions in any embodiments described herein can be specifically formulated and suitable for PD or similar dialysis therapies. The dialysis solutions can be used, for example, as a single dialysis solution in a single container or as two or more dialysis parts of a separately housed or multi-chambered container. The dialysis solutions can be sterilized using any suitable sterilizing technique such as, for example, autoclave, steam, ultra-violet, high pressure, filtration or combination thereof.

Besides the glucose polymer, in any embodiments of the dialysis solutions described herein, the dialysis solutions can include one or more additional suitable dialysis components (e.g., ingredients or constituents of a dialysis solution) such as buffers, electrolytes or combination thereof. Non-limiting examples of the buffers include bicarbonate, lactic acid/lactate, pyruvic acid/pyruvate, acetic acid/acetate, citric acid/citrate, amino acids, peptides, an intermediate of the KREBS cycle and/or the like and combinations thereof.

Non-limiting examples of electrolytes include calcium, magnesium, sodium, potassium, chloride and/or the like and combinations thereof. For example, the dialysis solutions can include one or more electrolytes in the following ranges from: about 120 to about 146 mM of $Na^+$, about 90 to about 112 mM of $Cl^-$, about 0.25 to about 2.0 mM of $Ca^{2+}$, and/or about 0.125 to about 1.0 mM of $Mg^{2+}$. In another embodiment, the dialysis solutions can include potassium in an amount ranging from about 0.1 to about 4.5 mM of $K^+$. Any suitable electrolytes and amounts thereof can also be included in the first dialysis part and/or the second dialysis part of the multi-part dialysis solutions so as to provide a mixed final solution having the electrolyte concentrations described above.

In a multi-part dialysis solution in any of the embodiments described herein, the first dialysis part can contain the glucose polymer and include one or more physiological acceptable acids such as lactic acid, pyruvic acid, acetic acid, citric acid, hydrochloric acid or the like to provide a suitable pH. Alternatively, the pH can be adjusted without the use of acids by bubbling $CO_2$ in the solution. In any embodiments of the dialysis solutions described herein, the first part can have a pH ranging from about 3.5 to about 5.5 including 3.5, 4, 4.5, 5, 5.5 and any suitable pH within this range. In this regard, the degradation of the glucose polymer can be minimized during heat sterilization. It should be appreciated that these acids can also be used to modify the pH of any single container dialysis solutions described herein.

In a multi-part dialysis solution in any of the embodiments described herein, the second dialysis part can include a variety of different and suitable materials. For example, the second dialysis part can include a buffer solution providing a pH ranging from about 7 to about 9 including 7. 7.5, 8, 8.5, 9 and any suitable pH within this range. The buffer solution can include, for example, sodium bicarbonate, sodium chloride, sodium lactate, one or more amino acids with a pK between 7 and 13, such as histidine, glycine, alanine, etc., or combinations thereof. It should be appreciated that these bases can also be used to modify the pH of any single container dialysis solutions.

The separate dialysis parts of a multi-part dialysis solution can be housed or contained in any suitable manner such that the individual dialysis parts can be effectively prepared and administered. A variety of containers can be used to house the two parts, such as separate containers (e.g., flasks or bags) that are connected by a suitable fluid communication mechanism. The two or more separate dialysis parts can be separately sterilized and stored. The first dialysis part and the second dialysis part can be constructed and arranged that at least the first dialysis part and the second dialysis part are mixed prior to infusion into a patient. For example, the first dialysis part is stored in a first chamber of a multi-chamber container and the second dialysis part is stored in a second chamber of the multi-chamber container. By way of further example, the solutions can be provided separately as concentrates and a mixing device, such as the BAXTER HOMECHOICE® PD cycler, can be used to mix the solutions immediately prior to infusion.

Further, the multiple chamber container can be configured such that one of the dialysis parts can be placed in direct fluid communication with the patient prior to mixing while the other dialysis part cannot be placed in direct fluid communication with the patient prior to mixing. This can provide an added level of safety with respect to the preparation and administration of the ready-to-use foiinulation of the present disclosure as the single solution cannot be placed in direct fluid communication with the patient or administered to the patient unless it is first mixed with the other component. In this regard, if, by chance, the single solution part that physically cannot be placed in direct fluid communication with the patient were to have an undesirable concentration of constituents, such as potassium, sodium or the like, this configuration would necessarily ensure that the undesirable level of constituents is not administered to the patient.

In an alternative embodiment, the present disclosure provides an improved method of providing PD to a patient in need of same. The method includes providing a dialysis solution having a glucose polymer at a specified Mw, PolyD index and concentration that is improved in accordance with the present disclosure. The dialysis solution can then be administered to the patient using any suitable dialysis technique. For example, the dialysis solutions can be used during PD, such as automated PD, continuous ambulatory PD, continuous flow PD and the like.

Although the present disclosure, in an embodiment, can be utilized in methods providing a dialysis therapy for patients having chronic kidney failure or disease, it should be appreciated that the present disclosure can also be used for acute dialysis needs, for example, in an emergency room setting. Lastly, as one of skill in the art appreciates, the intermittent forms of dialysis therapy may be used in the in-center, self/limited care as well as the home settings.

EXAMPLES

By way of example and not limitation, the following examples are illustrative of various embodiments of the present disclosure. All concentrations ranges described herein are by weight percentage unless indicated otherwise.

Example 1

Computer Modeling

Computer Algorithms

A mathematical computer model of peritoneal transport based on PD ADEQUEST® (see E. F. Vonesh, et al., *Perit. Dial. Int.*, 26: 475-81, 2006) was developed to determine the criticality of glucose polymers having a specific combination of characteristics including Mw, PolyD and concentration on the performance of PD solutions containing glucose polymers as the osmotic agent. The mathematical computer model incorporates all major pathways involved in peritoneal fluid and solute transport; however, it assumes no metabolism of glucose polymers within the peritoneal cavity. This was a general approach and could be applied to any glucose polymer Mw fraction.

The current study evaluated specific glucose polymer Mw fractions with a variety of different physicochemical properties as long dwell osmotic agents to replace conventional dialysis solutions containing icodextrin as the API and improve PD solution performance. The molecular weight distribution of each glucose polymer Mw fraction was characterized by a Mw and a number-average molecular weight ("Mn"). Further, each glucose polymer Mw fraction was approximated by ten glucose polymer monomers. The molecular weights and concentrations of the ten glucose polymer monomers were adjusted such that the combination was equivalent to the glucose polymer Mw fraction with respect to Mw and Mn, assuming a molecular weight distribution that was log-normal. For calculating the peritoneal transport parameters of each hypothetical molecule according to a three-pore model, the molecular radius ("R") was calculated using the formula: $R=0.486 \times Mw^{0.385}$, (see B. Rippe and G. Stelin, *Kidney Int.*, 35:1234-1244, 1989). The PolyD index of each glucose polymer Mw fraction was calculated as the ratio of Mw to Mn.

Patients Modeled

Three PD patients (see E. F. Vonesh, et al., *Perit. Dial. Int.* 26: 475-81 (2006)) were used to characterize the effect of glucose polymer Mw fraction, PolyD and concentration on net UF volume and CHO absorption for patients with different peritoneal transport characteristics. These patients were chosen to represent low-average, high-average and high transport patients because their UF profiles (i.e., net UF volume vs. time curves) were considered representative of such patients. Small solute transport characteristics were previously evaluated to permit determination of the three-pore model parameters for each patient. Net UF volumes, but not absolute amounts of CHO absorption, calculated using PD ADEQUEST® 2.0 for EXTRANEAL® dialysis solution formulations (having 7.5% icodextrin) were validated during an 8-hour dwell. It was anticipated, however, that the current modeling approach would yield relative differences in CHO absorption that were realistic.

Computer Simulations

Each of the three patients was modeled using various glucose polymer Mw fractions with different Mw, PolyD index and concentration. The dwell time was fixed at 12 hours for all simulations, and the results from each simulation were net UF volume (in mL) and the amount of CHO absorbed (in grams). The glucose polymer, icodextrin, having the characteristics of a Mw=15.436 kdaltons ("K") and PolyD index=2.6 was used as the baseline or reference. Computer simulations were performed using icodextrin-based dialysis solutions having icodextrin concentrations ranging between 7.5% and 17.0% as a reference thereby representing PD solutions that could be formulated using the current commercial API.

Glucose polymer Mw fractions with various Mw, PolyD indexes and concentrations were computed over the following ranges: 1) Mw: Every 1K between 1 and 24 K, 2) PolyD index: 1.6, 1.8, 2.0 2.2 2.4, and 3) Concentration: 5.0-15.0%. The net UF volume and CHO absorption for each glucose polymer Mw fraction was compared with that for all reference icodextrin solutions with concentrations between 7.5% and 17.0%.

A glucose polymer Mw fraction at a given PolyD index and concentration was considered to have superior performance compared with the referent icodextrin solution if it produced a higher net UF volume than any referent icodextrin solution and an absorption of CHO not greater from a clinical perspective than that for the same referent icodextrin solution. With respect to CHO absorption, clinical significance was defined as CHO absorption not different by more than 3 grams. This differential was chosen because a difference of 3 grams of CHO absorption was not measurable in a representative clinical trial (see J. Plum, et al., *Am J Kidney Dis.*, 39:862-871, 2002); a differential of at least 5 grams of CHO absorption would be necessary to permit the detection of a clinically meaningful difference. The determination of the increased UF fluid volume for a given amount of CHO absorbed of the dialysis solutions based on specific combinations of glucose polymer Mw fractions, PolyD index and concentration in accordance with embodiments of the present disclosure was based on computer simulations using the PD ADEQUEST® model.

EXTRANEAL® Dialysis Solution Formulation Performance

A commercial glucose polymer-based dialysis solution on the market is EXTRANEAL® dialysis solution. EXTRANEAL® dialysis solution is a peritoneal dialysis solution containing the osmotic agent icodextrin at a 7.5% concentration. The PolyD index of this polymer fraction is 2.6 or greater.

Figure 1:
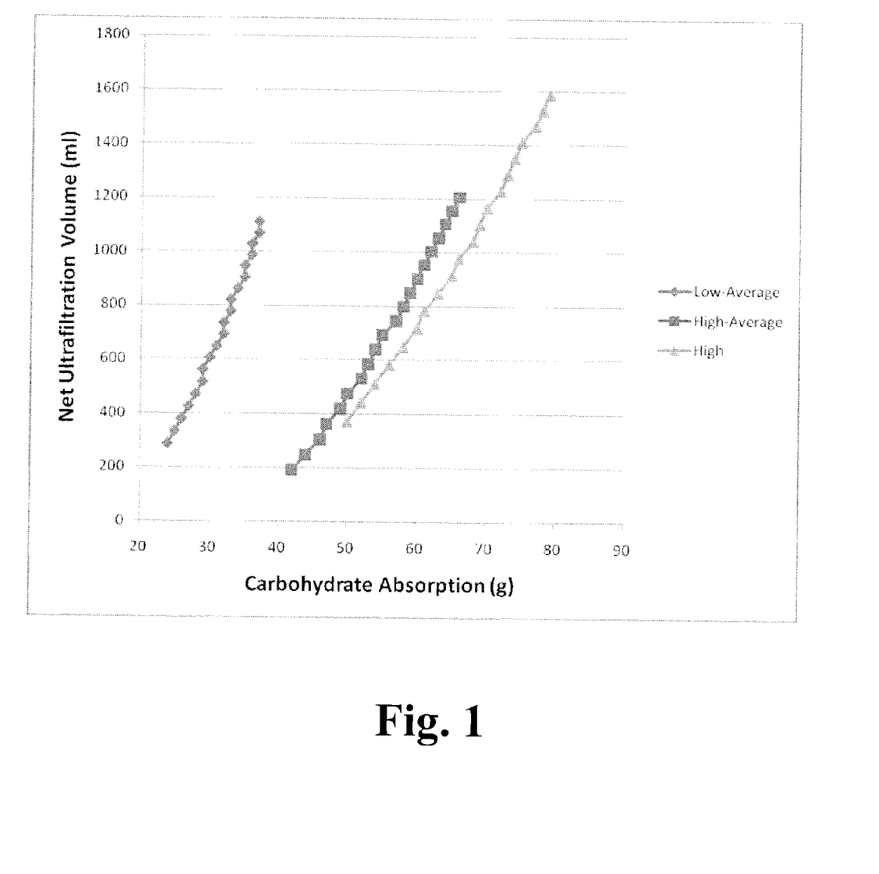
FIG. 1 shows a graph of the predicted effect of increasing the glucose polymer concentration on the performance of PD solutions containing the glucose polymer icodextrin for three different patient types—a high ("H") transporter, high-average ("HA") transporter and low-average ("LA") transporter using a computer model.

In FIG. 1, the effect of increasing the glucose polymer concentration on the performance of PD solutions containing the glucose polymer icodextrin used in the EXTRANEAL® dialysis solutions is simulated using the computer model. The predicted values for net UF and CHO absorption were obtained for three different patient types, one each for a high ("H") transporter, high-average ("HA") transporter and low-average ("LA") transporter. Generally, as the icodextrin concentrations increased, the net UF volume and CHO absorption increased as well for the three different PD patients.

These results are important because they describe the baseline performance of the standard commercial EXTRANEAL® dialysis solution and potential solutions containing the same glucose polymer (i.e., icodextrin) at different concentrations. An improved PD solution containing critical ranges of glucose polymer Mw fractions when plotted in the same manner will lie above the icodextrin-based solutions curve for a given patient. Similar plots were made when displaying results of various glucose polymer Mw fractions from computer modeling studies.

The inventors surprisingly discovered that modifying the characteristics of the glucose polymer Mw distribution (Mw and PolyD index) for certain concentrations resulted in increased net UF with equal or less CHO absorption as compared with the icodextrin-based dialysis solution. The varying glucose polymer Mw fractions ranged in concentration from 5% to 15% w/v.

Preliminary Computer Simulation Results

Figure 2:
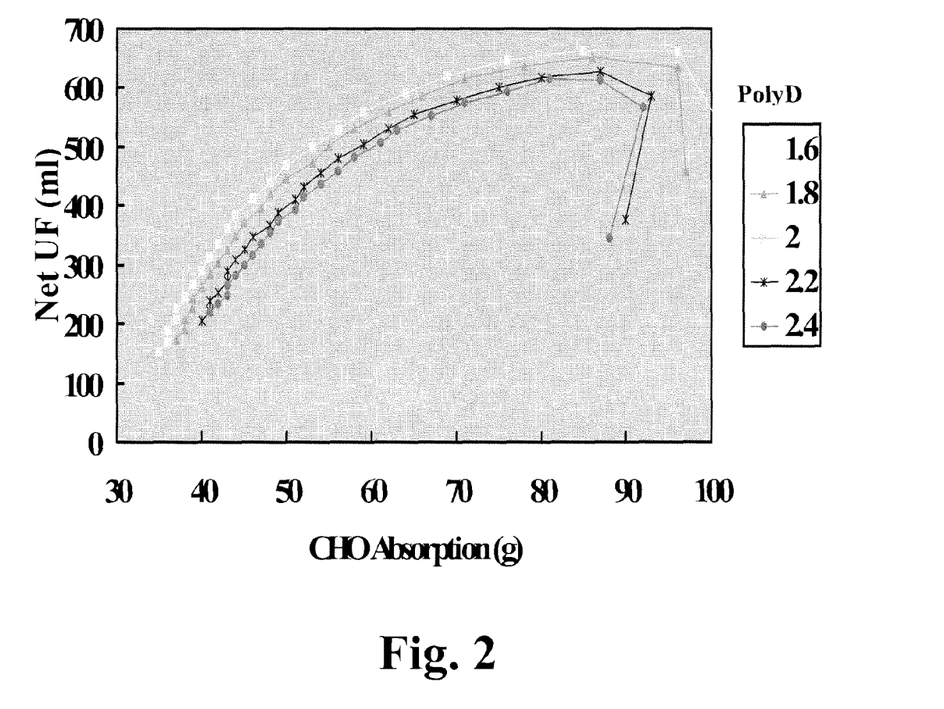
FIG. 2 shows a graph of the predicted net UF versus CHO absorption for glucose polymer Mw fractions with Mw for every 1K from 24K to 1K (data points from left to right) and at different PolyD indexes for a high transport patient using a computer model. The concentration of the glucose polymer was identical at 7.5% for each Mw fraction.

This study examined whether Mw and PolyD index impacts the relationship between net UF and CHO absorption for glucose polymer Mw fractions at a specific glucose polymer concentration. The results shown in FIG. 2 are a plot of net UF versus CHO absorption for the glucose polymer Mw fractions having various PolyD indexes with glucose polymer Mw fractions ranging from 24K to 1K (plotted data points in 1K intervals from left to right) for a high transport patient. Each glucose polymer Mw fraction studied here was at a fixed concentration of 7.5%. Dwell time was 12 hours.

It was found that glucose polymer fractions with higher Mw generally yielded the lowest net UF and had the lowest CHO absorption. The glucose polymer fractions with lower Mw generally yielded the highest net UF and the higher CHO absorption. Lowering the glucose polymer Mw fraction to about 2 K increased net UF for a given CHO absorption at most evaluated PolyD indexes (PolyD indexes=1.6, 1.8, 2.0, 2.2 and 2.4). For a given CHO absorption, a lower glucose polymer PolyD index generally required a lower Mw of the glucose polymer Mw fraction. This effect of specific glucose polymer PolyD index in combination with Mw and concentration formed the basis for altering glucose polymer Mw distribution to increase the UF fluid volume for a given amount of CHO absorbed for dialysis solutions containing the glucose polymers.

Figure 3:
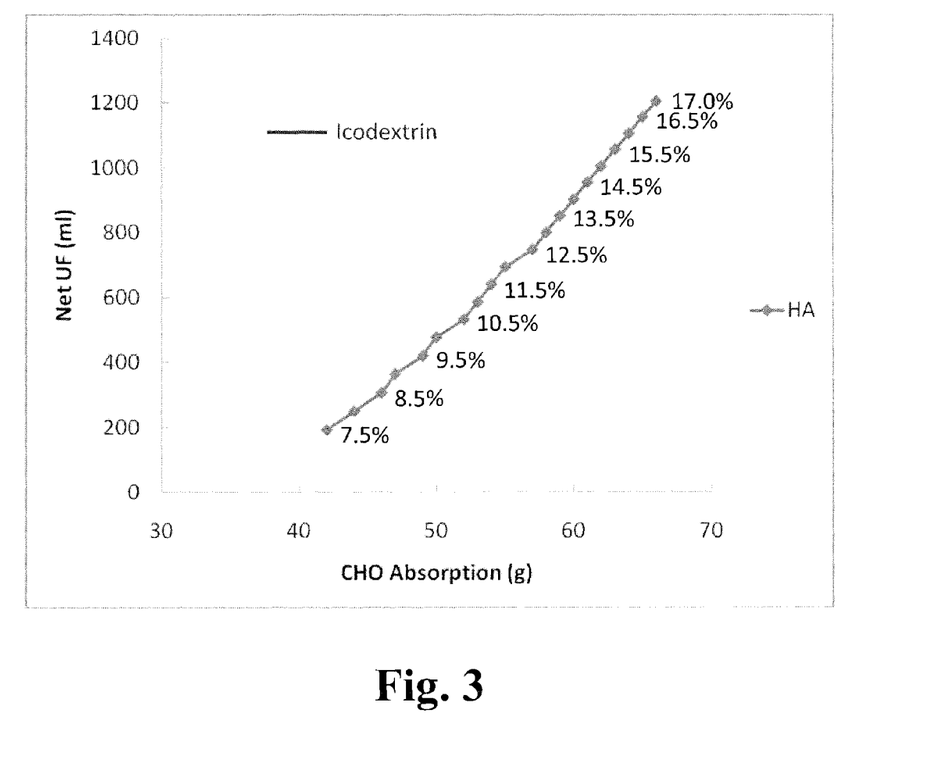
FIG. 3 shows a graph of the predicted net UF versus CHO absorption of icodextrin-based solution formulations at different concentrations of the glucose polymer in an HA transport patient using a computer model.

A range of glucose polymer Mw fractions were found and compared to the performance of the icodextrin-based dialysis solutions using the computer simulation studies. The computer simulations of the net UF volume versus CHO absorption in an HA transport patient of the icodextrin-based dialysis solution at concentrations ranging from 7.5% to 17% are indicated by the solid line in FIG. 3. From FIG. 3, combinations of Mw, PolyD index and concentration of the glucose polymers that, when plotted in this fashion, result in points above the solid line are glucose polymer Mw fractions having an increased UF fluid volume for a given amount of CHO absorbed over the icodextrin-based dialysis solutions. Similar analysis was performed for other patient types and other glucose polymer Mw fractions as discussed below. These principles were used in evaluating computed net UF versus CHO absorption plots for the tested glucose polymer Mw fractions.

Detailed Simulation Results

Computer simulations were performed for dialysis solutions including glucose polymer Mw fractions with PolyD indexes of 1.6, 1.8, 2.0, 2.2 and 2.4 in an H transport patient, an HA transport patient and an LA transport patient. The Mw ranged from 1 K to 24 K and the glucose polymer Mw fractions ranged in concentration from 5% to 15% by weight for each patient type.

Tables 1A and 1B show the concentration ranges where various glucose polymer Mw fractions at the indicated Mw and PolyD index achieved greater net UF volume without greater absorption of CHO from a clinical perspective compared with when icodextrin as the API is used. The concentration ranges reported apply to low-average, high-average and high transport patients. For example, a 15K glucose polymer Mw fraction was found to achieve superior performance to the icodextrin-based dialysis solution at concentrations of 8.5% or greater up to 15.0% for PolyD indexes of 1.6 and 1.8 and of 8.0% or greater up to 15% for PolyD indexes of 2.0, 2.2 and 2.4.

In general, decreasing the PolyD index of the glucose polymer to less than or equal to about 2.4 provides PD solutions that achieve an increased UF fluid volume for a given amount of CHO absorbed than the icodextrin-based dialysis solution at the Mw and concentrations listed in Tables 1A and 1B.

If the concentration of the glucose polymer Mw fraction is increased above about 7.5%, several additional glucose polymer Mw fractions having a PolyD index of about 2.0 also have a significant increased UF fluid volume for a given amount of CHO absorbed compared to the icodextrin-based dialysis solution. These include: a) 15K glucose polymer Mw fraction at a concentration equal to or greater than about 8.0%; b) 17K glucose polymer Mw fraction at a concentration equal to or greater than about 8.5% and the c) 18K and 19K glucose polymer Mw fractions at a concentration equal to or greater than about 9.0%.

Conclusions

Computer modeling simulations have shown that dialysis solutions including novel glucose polymer combinations of Mw, PolyD index and concentration achieve higher UF at the same or lower CHO absorption as compared with conventional dialysis solutions containing icodextrin as the API.

Example 2

Animal Studies

Evaluation of 18K and 19K Glucose Polymer Mw Fractions in a Rabbit Model

Computer modeling suggested that a 9.0-15.0% w/v concentration of the 18-19K glucose polymer Mw fraction with a PolyD index of about 2.0 would provide enhanced net UF relative to an icodextrin-based dialysis solution without significant increase in CHO absorption, i.e., an increase in UF efficiency (the ratio of net UF to CHO absorption). The studies described here were undertaken to evaluate the performance of a 10-11% solution of the 19K glucose polymer Mw

TABLE 1A

| PolyD index | Weight-average Molecular Weight | | | | | | | | | | | |
|---|---|---|---|---|---|---|---|---|---|---|---|---|
| | 1K | 2K | 3K | 4K | 5K | 6K | 7K | 8K | 9K | 10K | 11K | 12K |
| 1.6 | | | | | | | | 7.0-10.0 | 7.0-15.0 | 7.0-15.0 | 7.5-15.0 | 8.0-15.0 |
| 1.8 | | | | | | | | | 7.0-11.0 | 7.0-15.0 | 7.5-15.0 | 7.5-15.0 |
| 2.0 | | | | | | | | | | 7.0-13.0 | 7.0-15.0 | 7.5-15.0 |
| 2.2 | | | | | | | | | | | 7.0-11.0 | 7.5-15.0 |
| 2.4 | | | | | | | | | | | | 7.5-12.0 |

TABLE 1B

| PolyD index | Weight-average Molecular Weight | | | | | | | | | | | |
|---|---|---|---|---|---|---|---|---|---|---|---|---|
| | 13K | 14K | 15K | 16K | 17K | 18K | 19K | 20K | 21K | 22K | 23K | 24K |
| 1.6 | 8.0-15.0 | 8.5-15.0 | 8.5-15.0 | 9.0-15.0 | 9.0-15.0 | 9.5-15.0 | 9.5-15.0 | 10.0-15.0 | 10.0-15.0 | 10.0-15.0 | 10.5-15.0 | 13.0-15.0 |
| 1.8 | 8.0-15.0 | 8.0-15.0 | 8.5-15.0 | 9.0-15.0 | 9.0-15.0 | 9.0-15.0 | 9.0-15.0 | 9.5-15.0 | 9.5-15.0 | 10.0-15.0 | 10.0-15.0 | 10.5-15.0 |
| 2.0 | 7.5-15.0 | 8.0-15.0 | 8.0-15.0 | 8.5-15.0 | 8.5-15.0 | 9.0-15.0 | 9.0-15.0 | 9.0-15.0 | 9.5-15.0 | 9.5-15.0 | 10.0-15.0 | 10.0-15.0 |
| 2.2 | 7.5-15.0 | 7.5-15.0 | 8.0-15.0 | 8.0-15.0 | 8.5-15.0 | 8.5-15.0 | 9.0-15.0 | 9.0-15.0 | 9.0-15.0 | 9.5-15.0 | | |
| 2.4 | 7.5-15.0 | 7.5-15.0 | 8.0-15.0 | 8.0-15.0 | 8.0-15.0 | 8.5-15.0 | 8.5-15.0 | 9.0-15.0 | 9.0-15.0 | 9.0-15.0 | 9.5-15.0 | 10.0-15.0 |

The calculated results from Tables 1A and 1B demonstrate that there exist novel combinations of glucose polymer Mw fraction, PolyD index and concentration that achieve superior performance compared with icodextrin. These novel combinations result from both the physicochemical properties of the glucose polymers and patient transport characteristics.

fraction with a PolyD index of about 2.0; the conclusions of these studies were then confirmed by evaluating the performance of an 11% solution of an 18K glucose polymer Mw fraction with a PolyD index of about 2.0.

Study Design

Female New Zealand white rabbits (2.4-2.8 kg) with an implanted peritoneal catheter were used in these studies (N=8-9 per group). Solutions containing either an 18K glucose polymer Mw fraction, a 19K glucose polymer Mw fraction, an EXTRANEAL® dialysis solution formulation containing icodextrin at 7.5% concentration or a conventional dialysis solution containing icodextrin as the API at 11% concentration were infused into the rabbit peritoneal cavity at a dose of 40 mL/kg body weight for either a 4 hour or an 8 hour dwell. Five studies were performed (see Tables 2-3 for experimental details).

TABLE 2

| Study | 19K[1]/18K[2] solution | Dwell Time | N/group | Controls (concentration w/v) |
|---|---|---|---|---|
| 1 | 10% | 4 hr | 8 | EXTRANEAL ® (7.5%) control |
| 2 | 11% | 8 hr | 9 | EXTRANEAL ® (7.5%) control, RISA added as a volume marker |
| 3 | 11% | 8 hr | 9 | EXTRANEAL ® (7.5%) control |
| 4 | 11% | 8 hr | 9 | Icodextrin-based dialysis solution (11%) control |
| 5 | 11%[2] | 8 hr | 12 | EXTRANEAL ® (7.5%) control |

[1]19K glucose polymer Mw fraction (Mw = 18,807 Daltons, PolyD index = 2.06).
[2]18K glucose polymer Mw fraction (Mw = 18,048 Daltons, PolyD index = 1.98) used in Study #5.

TABLE 3

| Formulations | |
|---|---|
| Ingredient (unit) | Amount |
| Glucose polymer (18K or 19K) or icodextrin-based dialysis solution (g/L) | 100-110 |
| Calcium (mmol/L) | 1.75 |
| Magnesium (mmol/L) | 0.25 |
| Sodium (mmol/L) | 132 |
| Potassium (mmol/L) | 0 |
| Chloride (mmol/L) | 96 |
| Lactate (mmol/L) | 40 |

In order to accommodate the surgical procedures and the effluent collection for studies 2-5, the rabbits were assigned to one of two blocks with blocks staggered by one day. The rabbits in each block were randomly assigned into 2 treatment groups. For each of the studies conducted, Group 1 was designated the control group (EXTRANEAL® dialysis solution formulation or icodextrin-based dialysis solution at a concentration of 11%) and Group 2 was designated the test group (18K glucose polymer Mw fraction or 19K glucose polymer Mw fraction). The studies were conducted over a two-day period. On day one (Block 1), approximately half of the animals in Group 1 and approximately half of the animals in Group 2 were tested. On the second day (Block 2), the remainder of the animals in Group 1 and Group 2 were tested.

On the day of the PD dwell, the rabbits were weighed for the dose calculation and the appropriate solution was administered via an intraperitoneal ("IP") catheter. Rabbit infusions were staggered by 10 minutes in order to accommodate the necropsy procedure and were alternated between treatment groups (i.e., Group 1, Group 2, Group 1, Group 2, and so on) until all of the animals were placed on study.

In Study 1, a 10% (w/v) solution of the 19K glucose polymer Mw fraction with a Mw of 18,807 Daltons and a PolyD index of 2.06 was evaluated using a 4-hour dwell. In Study 2, the dwell time was extended to 8-hours and radio-iodinated serum albumin ("RISA"), a volume marker, was used to determine the intraperitoneal volume profile over time. For this study, an 11% (w/v) solution of the 19K glucose polymer Mw fraction was used. Two 8-hour dwell studies were then performed with an 11% solution of the 19K glucose polymer Mw fraction using either the EXTRANEAL® dialysis solution formulation (Study 3) or the icodextrin-based dialysis solution at a concentration of 11% (Study 4) as controls.

An 18K glucose polymer Mw fraction with a Mw of 18,048 Daltons and a PolyD index of 1.98 was used at 11% w/v concentration and compared with the EXTRANEAL® dialysis solution formulation (7.5% w/v concentration of icodextrin) in Study 5. This study was identical in design to Study 3 except that the 18K glucose polymer Mw fraction was used instead of the 19K glucose polymer Mw fraction. In each of the 5 studies, the animals were sacrificed at the end of the dwell period. Net UF was determined by subtracting the infused volume from the measured effluent volume, and the absorption of the glucose polymer determined by subtracting the glucose polymer mass infused (concentration times volume) from the glucose polymer mass in the effluent.

Results

Figure 4:
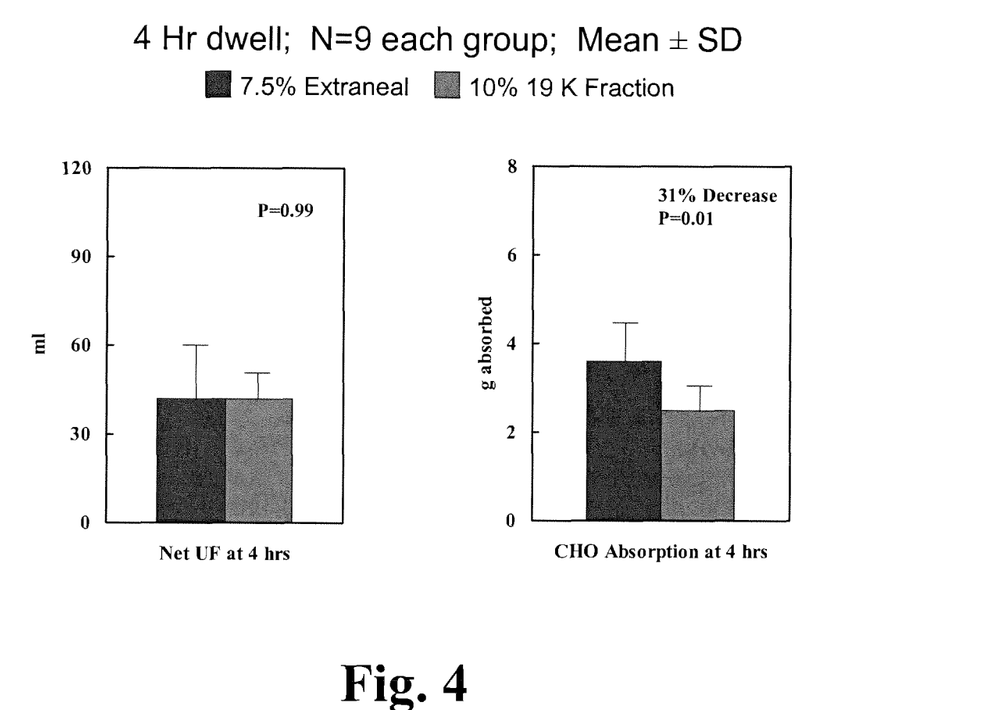
FIG. 4 shows the results of Study 1: 19K glucose polymer Mw fractions vs. the EXTRANEAL® dialysis solution formulation at a 4 hour dwell time.

In Study 1, the net UF achieved with the 10% solution of the 19K glucose polymer Mw fraction was similar to that achieved with the EXTRANEAL® dialysis solution formulation (41.9 mL vs. 42.0 mL, P=0.99) (FIG. 4). However, the CHO absorption for the 19K glucose polymer Mw fraction was 31% lower than that observed with the EXTRANEAL® dialysis solution formulation (P=0.01). These observations show that a dialysis solution containing a 19K glucose polymer Mw fraction with a PolyD index of about 2.0 at a concentration of 10% has a higher UF efficiency than the EXTRANEAL® dialysis solution formulation as predicted by the computer simulations. The increase in net UF was not as large as predicted by the computer simulations however. This may be due in part to higher levels of intraperitoneal amylase (the enzyme that metabolizes glucose polymers) in the rabbit versus those found in PD patient effluent coupled with the inherent differences in the peritoneal membrane of rabbits versus humans. To overcome such limitations, the remainder of the rabbit experiments were performed using higher concentrations (11% instead of 10%) of the 18K and 19K glucose polymer Mw fractions. The experimental dwell was also extended from 4 to 8 hours to be more similar to long dwells in human PD patients.

Figure 5:
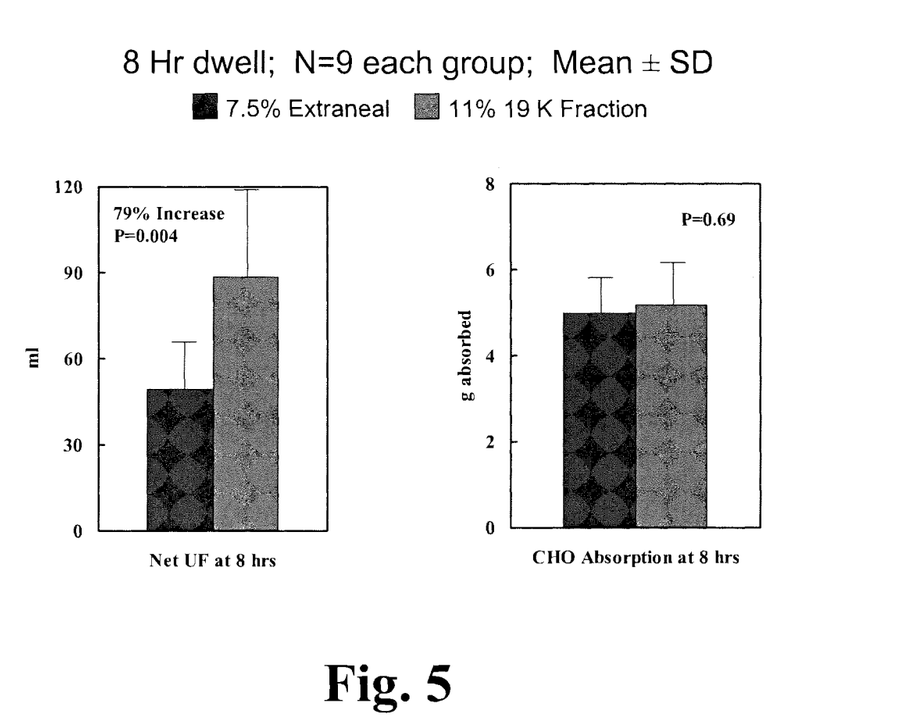
FIG. 5 shows the results of Study 3: 19K glucose polymer Mw fractions vs. the EXTRANEAL® dialysis solution formulation at an 8 hour dwell time.

In Study 3, with the dwell time extended to 8 hours and the concentration of the 19K glucose polymer Mw fraction increased slightly to 11%, the net UF provided by the 19K glucose polymer Mw fraction was significantly larger than when using the EXTRANEAL® dialysis solution formulation (88.6 mL vs. 49.3 mL, P=0.004) (FIG. 5). The CHO absorption was not significantly different between the 2 solutions (P=0.69).

The improved UF at 8 hours provided by the 19K glucose polymer Mw fraction vs. the EXTRANEAL® dialysis solution formulation was also demonstrated in Study 2 with the use of RISA as a volume marker. In this study, the 19K glucose polymer Mw fraction provided a 42% increase in net UF after 8 hours over the EXTRANEAL® dialysis solution formulation (50.1 mL vs. 35.4 mL). The intraperitoneal volume profiles determined over the course of the dwell suggests that the improvement in net UF provided by the 19K glucose polymer Mw fraction becomes apparent after 4 hours, and confirms the trends in UF observed in Studies 1 and 3.

Study 4 was performed comparing the 19K glucose polymer Mw fraction with the 11% icodextrin-based dialysis solution over an 8-hour dwell. The 19K glucose polymer Mw fraction net UF was 68.2 mL vs. 56.8 mL obtained with the 11% icodextrin-based dialysis solution. In addition, the CHO absorption was higher with the 11% icodextrin-based dialysis solution as compared with the 19K glucose polymer Mw fraction. These results are summarized in Table 4. The combined results from these animal experiments demonstrate that glucose polymers with unique combinations of Mw and PolyD index have advantages when compared with icodextrin as an osmotic agent.

TABLE 4

CHO Absorption & UF Efficiency - 8 Hours

| Solution | % | Glucose Polymer Infused (g) | Glucose Polymer Absorbed (g) | % Glucose Polymer Absorbed | Net UF (ml ± SD) | UF Efficiency (ml/g) |
|---|---|---|---|---|---|---|
| 19K | 11% | 11.36 | 5.3 | 46.6 | 68.2 ± 20 | 13.2 |
| Icodextrin | 11% | 11.06 | 6.4 | 57.1 | 56.8 ± 15 | 9.3 |
| — | — | — | P = 0.0313 | P = 0.0168 | P = 0.2042 | P = 0.0608 |

Study 5 was performed comparing an 18K glucose polymer Mw fraction with the EXTRANEAL® dialysis solution formulation over an 8-hour dwell. The 18K glucose polymer Mw fraction net UF was 96 mL vs. 66 mL obtained with the EXTRANEAL® dialysis solution formulation. In addition, the CHO absorption was higher with the EXTRANEAL® dialysis solution formulation as compared to the 18K glucose polymer Mw fraction. The results are summarized in Table 5.

TABLE 5

CHO Absorption & UF Efficiency - 8 Hours

| Solution | % | Glucose Polymer infused (g) | Glucose Polymer absorbed (g) | % Glucose Polymer absorbed | Net UF (ml ± SD) | UF efficiency (ml/g) |
|---|---|---|---|---|---|---|
| 18K | 11 | 10.74 | 4.76 | 44.32 | 96 ± 18 | 20.7 |
| EXTRANEAL ® | 7.5 | 7.98 | 5.18 | 64.91 | 66 ± 17 | 13.0 |
| — | — | — | P = 0.1489 | P = 1.4e−7 | P = 0.0004 | P = 0.0006 |

The results from Study 5 confirmed those from Study 3, demonstrating that use of a 18K glucose polymer Mw fraction at 11% concentration results in higher net UF without an increase in CHO absorption compared with the EXTRANEAL® dialysis solution formulation during a long dwell exchange. Because the 18K and 19K fractions were produced in separate batches with similar, but not identical, molecular properties, this observation suggests that minor differences in manufacturing such fractions will not result in major differences in clinical performance.

Summary

Figure 6:
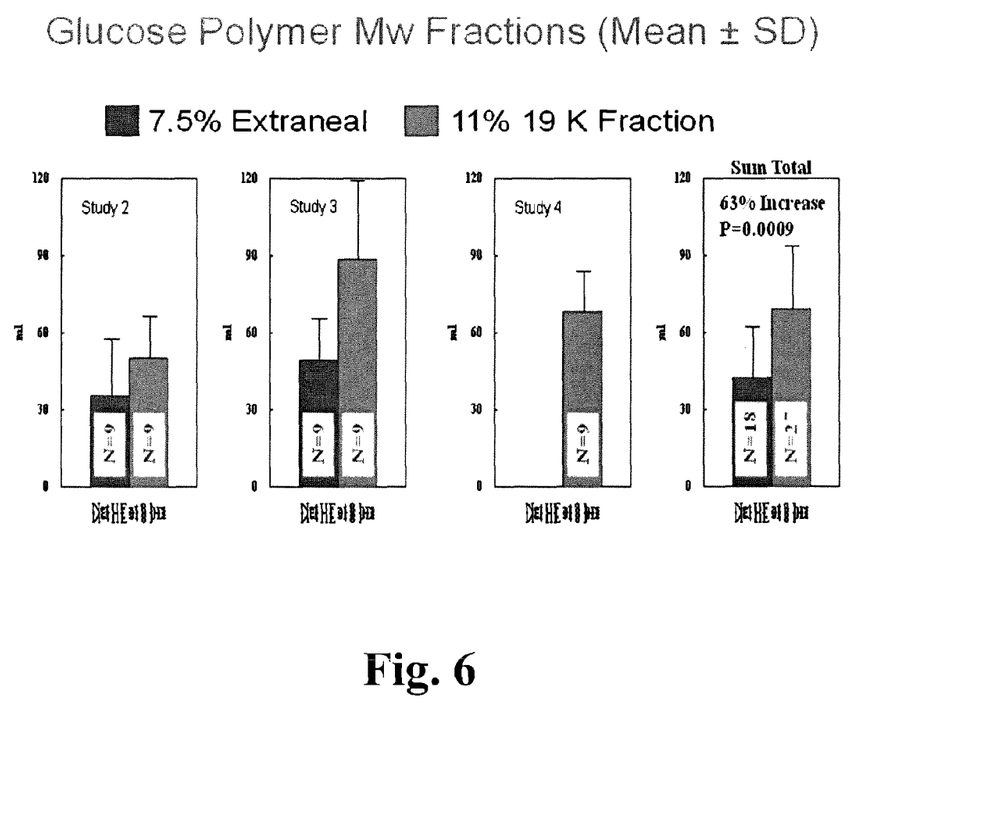
FIG. 6 shows a summary of Studies 2, 3 and 4 using 19K glucose polymer Mw fractions.

FIG. 6 shows a summary of Studies 2, 3 and 4 using the 19K glucose polymer Mw fraction. The results of these studies provide in vivo evidence for the concept of using a discrete molecular weight fraction of a glucose polymer to provide improved performance over a standard EXTRANEAL® dialysis solution or an 11% (w/v) icodextrin-based dialysis solution. Improved performance of the 19K glucose polymer Mw fraction over the EXTRANEAL® dialysis solutions or the icodextrin-based dialysis solution was demonstrated in the first four studies in terms of increased UF and/or UF efficiency. Further, the improvement in net UF and UF efficiency in Study 5 using the 18K glucose polymer Mw fraction indicates that two independently produced batches of glucose polymer Mw fraction material with similar molecular weight and PolyD index profiles resulted in identical performance as osmotic agents.

These studies also confirmed previous computer modeling efforts regarding the behavior of 18-19K glucose polymer Mw fractions, thereby providing strong support for the clinical application of such solutions. Collectively, the observations from these studies experimentally demonstrate that the 18K and 19K glucose polymer Mw fractions at a higher concentration and lower PolyD index than the current EXTRANEAL® dialysis solution formulation (e.g., 11% vs. 7.5%) provide a higher net UF without the penalty of increased CHO absorption. The 19K glucose polymer Mw fraction at a similar concentration (e.g., 11%) compared to the icodextrin-based dialysis solution provides a similar net UF while having a lower CHO absorption.

Example 3

Formulations

By way of example and not limitation, the following examples are illustrative of various embodiments of dialysis solution formulations having glucose polymers as described herein.

TABLE 6

Formulation #1 - Single Chamber

| Ingredient (unit) | Amount | Suitable Range |
|---|---|---|
| Glucose Polymer (g/L) | 100 | 70-150 |
| Calcium (mmol/L) | 1.75 | 0.25-2.0 |
| Magnesium (mmol/L) | 0.25 | 0.125-1.0 |
| Sodium (mmol/L) | 133 | 120-135 |
| Potassium (mmol/L) | 0 | 0-4.5 |
| Chloride (mmol/L) | 96 | 90-110 |
| Lactate (mmol/L) | 40 | 30-60 |
| pH | 5.5 | 5.0-6.0 |

TABLE 7

Formulation #2 - Two Chamber

| Ingredient (unit) | Amount | Suitable Range |
|---|---|---|
| Composition of Glucose Polymer Chamber | | |
| Glucose Polymer (grams) | 209 | 145-315 |
| Calcium Chloride dihydrate (mmol/L) | 4.83 | 0.5-10.0 |
| Magnesium chloride hexahydrate (mmol/L) | 0.69 | 0.5-2.0 |
| Potassium Chloride (mmol/L) | 0 | 0-13.5 |
| HCl for pH adjustment between 3.5 and 5.5 (mmol/L) | 0 | 0-10 |
| Solution volume (mL) | 758 | |
| Composition of Buffer Chamber | | |
| Sodium Chloride (mmol/L) | 141 | 50.0-150.0 |
| Sodium Lactate (mmol/L) | 63 | 50-120 |
| Potassium Chloride (mmol/L) | 0 | 0-13.5 |
| Sodium Bicarbonate for pH adjustment between 8.0 and 9.0 (mmol/L) | 3 | <5.0 |
| Solution volume (mL) | 1332 | |
| Composition of Mixed Solutions | | |
| Glucose Polymer (g/L) | 100 | 70-150 |
| Calcium (mmol/L) | 1.75 | 0.25-2.0 |
| Magnesium (mmol/L) | 0.25 | 0.125-1.0 |
| Sodium (mmol/L) | 132 | 120-135 |
| Potassium (mmol/L) | 0 | 0-4.5 |
| Chloride (mmol/L) | 94 | 90-110 |
| Lactate (mmol/L) | 40 | 30-45 |
| Bicarbonate (mmol/L) | 2 | <5.0 |
| Solution volume (mL) | 2090 | |

TABLE 8

Formulation #3 - Two Chamber

| Ingredient (unit) | Amount | Suitable Range |
|---|---|---|
| Composition of Glucose Polymer Chamber | | |
| Glucose Polymer (grams) | 209 | 145-315 |
| Calcium Chloride dihydrate (mmol/L) | 4.83 | 0.5-10.0 |
| Magnesium chloride hexahydrate (mmol/L) | 0.69 | 0.5-2.0 |
| Potassium Chloride (mmol/L) | 0 | 0-13.5 |
| HCl for pH adjustment between 3.5 and 5.5 (mmol/L) | 0 | 0-10 |
| Solution volume (mL) | 758 | |
| Composition of Buffer Chamber | | |
| Sodium Chloride (mmol/L) | 144 | 50.0-150.0 |
| Sodium Lactate (mmol/L) | 63 | 50-120 |
| Potassium Chloride (mmol/L) | 0 | 0-13.5 |
| Histidine for pH adjustment between 8.0 and 9.0 (mmol/L) | 0.6 | <5.0 |
| Solution volume (mL) | 1332 | |
| Composition of Mixed Solutions | | |
| Glucose Polymer (g/L) | 100 | 70-150 |
| Calcium (mmol/L) | 1.75 | 0.25-2.0 |
| Magnesium (mmol/L) | 0.25 | 0.125-1.0 |
| Sodium (mmol/L) | 132 | 120-135 |
| Potassium (mmol/L) | 0 | 0-4.5 |
| Chloride (mmol/L) | 96 | 90-110 |
| Lactate (mmol/L) | 40 | 30-45 |
| Histidine (mmol/L) | 0.4 | <5.0 |
| Solution volume (mL) | 2090 | |

TABLE 9

Formulation #4 - Two Chamber

| Ingredient (unit) | Amount | Suitable Range |
|---|---|---|
| Composition of Glucose Polymer Chamber | | |
| Glucose Polymer (grams) | 200 | 140-300 |
| Calcium Chloride dihydrate (mmol/L) | 3.5 | 2.0-4.0 |
| Magnesium chloride hexahydrate (mmol/L) | 1.0 | 0.8-1.2 |
| Sodium Chloride (mmol/L) | 190 | 180-200 |
| Potassium Chloride (mmol/L) | 0 | 0-13.5 |
| HCl for pH adjustment between 3.5 and 5.0 (mmol/L) | 0 | 0-10 |
| Solution volume (mL) | 1000 | |
| Composition of Buffer Chamber | | |
| Sodium Lactate (mmol/L) | 70 | 60-80 |
| Potassium Chloride (mmol/L) | 0 | 0-13.5 |
| Sodium bicarbonate | 1.0 | 0.5-2.0 |
| Solution volume (mL) | 1000 | |
| Composition of Mixed Solutions | | |
| Glucose Polymer (g/L) | 100 | 70-150 |
| Calcium (mmol/L) | 1.75 | 0.25-2.0 |
| Magnesium (mmol/L) | 0.5 | 0.125-1.0 |
| Sodium (mmol/L) | 130.5 | 120-135 |
| Potassium (mmol/L) | 0 | 0-4.5 |
| Chloride (mmol/L) | 99.5 | 90-110 |
| Lactate (mmol/L) | 35 | 30-45 |
| Solution volume (mL) | 2000 | |

TABLE 10

Formulation #5 - Two Chamber

| Ingredient (unit) | Amount | Suitable Range |
|---|---|---|
| Composition of Glucose Polymer Chamber | | |
| Glucose Polymer (grams) | 200 | 140-300 |
| Calcium Chloride dihydrate (mmol/L) | 2.75 | 2.48-3.03 |
| Magnesium chloride hexahydrate (mmol/L) | 0.39 | 0.35-0.43 |
| Sodium Lactate (mmol/L) | 5 | 4.5-5.5 |
| Sodium Chloride (mmol/L) | 128 | 115-141 |
| Potassium Chloride (mmol/L) | 0 | 0-4.5 |
| HCl for pH adjustment between 4.0 and 5.5 (mmol/L) | 0 | 0-10 |
| Solution volume (mL) | 1275 | |
| pH | 5.0 | 4.0-5.5 |
| Composition of Buffer Chamber | | |
| Sodium Chloride (mmol/L) | 45 | 40-50 |
| Sodium Lactate (mmol/L) | 18.8 | 16.9-20.7 |
| Sodium Bicarbonate (mmol/L) | 70 | 63-77 |
| Potassium Chloride (mmol/L) | 0 | 0-4.5 |
| $CO_2$ for pH adjustment | | |
| Solution volume (mL) | 725 | |
| pH | 7.6 | 7.2-8.5 |
| Composition of Mixed Solution | | |
| Icodextrin (g/L) | 100 | 70-150 |
| Calcium (mmol/L) | 1.75 | 1.57-1.93 |
| Magnesium (mmol/L) | 0.25 | 0.225-0.275 |
| Sodium (mmol/L) | 133 | 120-146 |
| Chloride (mmol/L) | 102 | 92-112 |
| Potassium (mmol/L) | 0 | 0-4.5 |
| Lactate (mmol/L) | 10 | 9.0-11.0 |
| Bicarbonate (mmol/L) | 25 | 22.5-27.5 |
| Solution volume (mL) | 2000 | |
| pH | 7.4 | 7.0-8.0 |

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis solution comprising from about 7% w/v to about 10.5% w/v glucose polymer, the glucose polymer having a weight-average molecular weight of y and a polydispersity index of z, wherein y is from about 7,500 daltons to about 11,500 daltons and wherein:
    (a) if y=about 7,500 daltons to about 8,500 daltons, then z=about 1.5 to about 1.7;
    (b) if y=about 8,501 daltons to about 9,500 daltons, then z=about 1.7 to about 1.9; or
    (c) if y=about 10,500 daltons to about 11,500 daltons, then z=about 2.1 to about 2.3.

2. The dialysis solution of claim 1, wherein the dialysis solution comprises at least one additional dialysis component selected from the group consisting of buffers, electrolytes and combinations thereof.

3. The dialysis solution of claim 2, wherein the buffer is selected from the group consisting of bicarbonate, lactate, pyruvate, acetate, citrate, amino acids, peptides, an intermediate of a KREBS cycle and combinations thereof.

4. The dialysis solution of claim 2, wherein the electrolyte is selected from the group consisting of calcium, magnesium, sodium, potassium, chloride and combinations thereof.

5. The dialysis solution of claim 1, wherein the dialysis solution is sterilized.

6. A dialysis solution comprising from about 7% w/v to about 15% w/v glucose polymer, the glucose polymer having a weight-average molecular weight of y and a polydispersity index of z, wherein y is from about 9,500 daltons to about 13,500 daltons and wherein: (a) if y=about 8,500 daltons to about 9,500 daltons, then z =about 1.5 to about 1.7; (b) if y=about 9,501 daltons to about 10,500 daltons, then z=about 1.5 to about 1.9; (c) if y=about 10,501 daltons to about 11,500 daltons, then z=about 1.5 to about 2.1; (d) if y=about 11,501 daltons to about 12,500 daltons, then z=about 1.7 to about 2.3; or (e) if y=about 12,501 daltons to about 13,500 daltons, then z=about 1.9 to about 2.5.

7. The dialysis solution of claim 6, wherein the dialysis solution comprises at least one additional dialysis component selected from the group consisting of buffers, electrolytes and combinations thereof.

8. The dialysis solution of claim 7, wherein the buffer is selected from the group consisting of bicarbonate, lactate, pyruvate, acetate, citrate, amino acids, peptides, an intermediate of a KREBS cycle and combinations thereof.

9. The dialysis solution of claim 7, wherein the electrolyte is selected from the group consisting of calcium, magnesium, sodium, potassium, chloride and combinations thereof.

10. The dialysis solution of claim 6, wherein the dialysis solution is sterilized.

11. A dialysis solution comprising from about 8% w/v to about 15% w/v glucose polymer, the glucose polymer having a weight-average molecular weight of y and a polydispersity index of z, wherein y is from about 11,500 daltons to about 19,500 daltons and wherein: (a) if y=about 11,500 daltons to about 12,500 daltons, then z=about 1.5 to about 1.7; (b) if y=about 12,501 daltons to about 13,500 daltons, then z=about 1.5 to about 1.9; (c) if y=about 13,000 daltons to 14,000 daltons, then z=1.6-2.0; (d) if y=14,000 daltons to 15,000 daltons, then z=1.6-2.0; (e) if y=about 15,501 daltons to about 16,500 daltons, then z=about 1.7 to about 2.5; (f) if y=about 16,501 daltons to about 17,500 daltons, then z=about 1.9 to about 2.5; (g) if y=about 17,501 daltons to about 18,500 daltons, then z=about 2.1 to about 2.5; or (h) if y=about 18,501 daltons to about 19,500 daltons, then z=about 2.3 to about 2.5.

12. The dialysis solution of claim 11, wherein the dialysis solution comprises at least one additional dialysis component selected from the group consisting of buffers, electrolytes and combinations thereof.

13. The dialysis solution of claim 12, wherein the buffer is selected from the group consisting of bicarbonate, lactate, pyruvate, acetate, citrate, amino acids, peptides, an intermediate of a KREBS cycle and combinations thereof.

14. The dialysis solution of claim 12, wherein the electrolyte is selected from the group consisting of calcium, magnesium, sodium, potassium, chloride and combinations thereof.

15. The dialysis solution of claim 11, wherein the dialysis solution is sterilized.

16. A dialysis solution comprising from about 9% w/v to about 15% w/v glucose polymer, the glucose polymer having a weight-average molecular weight of y and a polydispersity index of z, wherein y is from about 15,500 daltons to about 23,500 daltons and wherein:
    (a) if y=about 15,501 daltons to about 16,500 daltons, then z=about 1.5 to about 1.7;
    (b) if y=about 16,501 daltons to about 17,500 daltons, then z=about 1.5 to about 1.9;
    (c) if y=about 17,501 daltons to about 18,500 daltons, then z=about 1.5 to about 2.1;
    (d) if y=about 18,501 daltons to about 19,500 daltons, then z=about 1.5 to about 2.3;
    (e) if y=about 19,501 daltons to about 20,500 daltons, then z=about 1.7 to about 2.5;
    (f) if y=about 20,501 daltons to about 21,500 daltons, then z=about 1.7 to about 2.5;
    (g) if y=about 21,501 daltons to about 22,500 daltons, then z=about 1.9 to about 2.5; or
    (h) if y=about 22,501 daltons to about 23,500 daltons, then z=about 2.3 to about 2.5.

17. The dialysis solution of claim 16, wherein the dialysis solution comprises at least one additional dialysis component selected from the group consisting of buffers, electrolytes and combinations thereof.

18. The dialysis solution of claim 17, wherein the buffer is selected from the group consisting of bicarbonate, lactate, pyruvate, acetate, citrate, amino acids, peptides, an intermediate of a KREBS cycle and combinations thereof.

19. The dialysis solution of claim 17, wherein the electrolyte is selected from the group consisting of calcium, magnesium, sodium, potassium, chloride and combinations thereof.

20. The dialysis solution of claim 16, wherein the dialysis solution is sterilized.

21. A dialysis solution comprising from about 10% w/v to about 15% w/v glucose polymer, the glucose polymer having a weight-average molecular weight of y and a polydispersity index of z, wherein y is from about 19,500 daltons to about 24,500 daltons and wherein:
- (a) if y=about 19,501 daltons to about 20,500 daltons, then z=about 1.5 to about 1.7;
- (b) if y=about 20,501 daltons to about 21,500 daltons, then z=about 1.5 to about 1.7;
- (c) if y=about 21,501 daltons to about 22,500 daltons, then z=about 1.5 to about 1.9;
- (d) if y=about 22,501 daltons to about 23,500 daltons, then z=about 1.5 to about 2.1; or
- (e) if y=about 23,501 daltons to about 24,500 daltons, then z=about 1.7 to about 2.1 or about 2.3 to about 2.5.

22. The dialysis solution of claim 21, wherein the dialysis solution comprises at least one additional dialysis component selected from the group consisting of buffers, electrolytes and combinations thereof.

23. The dialysis solution of claim 22, wherein the buffer is selected from the group consisting of bicarbonate, lactate, pyruvate, acetate, citrate, amino acids, peptides, an intermediate of a KREBS cycle and combinations thereof.

24. The dialysis solution of claim 22, wherein the electrolyte is selected from the group consisting of calcium, magnesium, sodium, potassium, chloride and combinations thereof.

25. The dialysis solution of claim 21, wherein the dialysis solution is sterilized.

26. A dialysis solution comprising from about 7% w/v to about 12.5% w/v glucose polymer, the glucose polymer having a weight-average molecular weight of y and a polydispersity index of z, wherein y is from about 9,500 daltons to about 12,500 daltons and wherein:
- (a) if y=about 9,500 daltons to about 10,500 daltons, then z=about 1.9 to about 2.1; or
- (b) if y=about 11,500 daltons to about 12,500 daltons, then z=about 2.3 to about 2.5.

27. The dialysis solution of claim 26, wherein the dialysis solution comprises at least one additional dialysis component selected from the group consisting of buffers, electrolytes and combinations thereof.

28. The dialysis solution of claim 27, wherein the buffer is selected from the group consisting of bicarbonate, lactate, pyruvate, acetate, citrate, amino acids, peptides, an intermediate of a KREBS cycle and combinations thereof.

29. The dialysis solution of claim 27, wherein the electrolyte is selected from the group consisting of calcium, magnesium, sodium, potassium, chloride and combinations thereof.

30. The dialysis solution of claim 26, wherein the dialysis solution is sterilized.

31. A dialysis solution comprising from about 13% w/v to about 15% w/v glucose polymer, the glucose polymer having a weight-average molecular weight of y and a polydispersity index of z, y is from about 23,500 daltons to about 24,500 daltons and wherein:
- (a) if y =about 23,500 daltons to about 24,500 daltons, then z =about 1.5 to about 1.7.

32. The dialysis solution of claim 31, wherein the dialysis solution comprises at least one additional dialysis component selected from the group consisting of buffers, electrolytes and combinations thereof.

33. The dialysis solution of claim 32, wherein the buffer is selected from the group consisting of bicarbonate, lactate, pyruvate, acetate, citrate, amino acids, peptides, an intermediate of the a KREBS cycle and combinations thereof.

34. The dialysis solution of claim 32, wherein the electrolyte is selected from the group consisting of calcium, magnesium, sodium, potassium, chloride and combinations thereof.

35. The dialysis solution of claim 31, wherein the dialysis solution is sterilized.

36. A method of preparing a dialysis solution, the method comprising:
selecting a specific Mw from a range of about 7,500 to about 24,500 daltons, a PolyD index and a w/v concentration of a glucose polymer to be used in the dialysis solution selected from a range of about 7% to about 15% w/v; and
providing the glucose polymer at the specified polydispersity index, molecular weight and w/v concentration in the dialysis solution according to claim 1, 6, 11, 16, 21, 26, or 31.

37. A method of providing dialysis to a patient in need thereof, the method comprising:
selecting a specific Mw from a range of about 7,500 to about 24,500 daltons, a PolyD index and a w/v concentration of a glucose polymer to be used in a dialysis solution selected from a range of about 7% to about 15% w/v;
providing the glucose polymer at the specified polydispersity index, molecular weight and w/v concentration in the dialysis solution according to claim 1, 6, 11, 16, 21, 26, or 31; and
administering the dialysis solution to the patient.

* * * * *